United States Patent
Grashow

(10) Patent No.: US 10,118,008 B2
(45) Date of Patent: Nov. 6, 2018

(54) MANIFOLD ASSEMBLY FOR RESPIRATORY INTERFACE DEVICE

(71) Applicant: KONINKLIJKE PHILIPS N.V., Eindhoven (NL)

(72) Inventor: Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 521 days.

(21) Appl. No.: 14/772,257

(22) PCT Filed: Feb. 26, 2014

(86) PCT No.: PCT/IB2014/059250
§ 371 (c)(1),
(2) Date: Sep. 2, 2015

(87) PCT Pub. No.: WO2014/136019
PCT Pub. Date: Sep. 12, 2014

(65) Prior Publication Data
US 2016/0008564 A1    Jan. 14, 2016

Related U.S. Application Data

(60) Provisional application No. 61/773,992, filed on Mar. 7, 2013.

(51) Int. Cl.
*A61M 16/06* (2006.01)
*A61M 16/08* (2006.01)
*A61M 39/10* (2006.01)

(52) U.S. Cl.
CPC ........ *A61M 16/06* (2013.01); *A61M 16/0683* (2013.01); *A61M 16/08* (2013.01);
(Continued)

(58) Field of Classification Search
CPC .. A61M 16/06; A61M 16/0683; A61M 16/08; A61M 16/0816; A61M 16/0666; A61M 39/1055; A61M 2210/0618; A61M 16/0633; A61M 16/0622; A61M 16/0605; A61M 16/0875; A61M 16/0611;
(Continued)

(56) References Cited

U.S. PATENT DOCUMENTS

| 5,538,000 A | 7/1996 | Rudolph |
|---|---|---|
| 6,039,044 A | 3/2000 | Sullivan |

(Continued)

FOREIGN PATENT DOCUMENTS

| CN | 101365508 A | 2/2009 |
|---|---|---|
| CN | 101380497 A | 3/2009 |

(Continued)

*Primary Examiner* — Andrew S Lo
(74) *Attorney, Agent, or Firm* — Michael W. Haas

(57) ABSTRACT

A respiratory interface device is provided. The respiratory interface device includes a manifold assembly including a manifold body and a rotational coupling. The manifold body includes an elastic portion. The rotational coupling includes a rigid conduit. The rigid conduit is rotatably coupled to the manifold body elastic portion. The rotational coupling and the elastic portion decouple the remaining portions of the manifold body from external forces applied to the rigid conduit.

16 Claims, 14 Drawing Sheets

(52) U.S. Cl.
CPC ..... *A61M 16/0816* (2013.01); *A61M 16/0666* (2013.01); *A61M 39/1055* (2013.01); *A61M 2210/0618* (2013.01)

(58) Field of Classification Search
CPC ............ A61M 16/0655; A61M 16/065; A61M 16/0644; A61M 2205/0216
USPC ................................................... 128/206.21
See application file for complete search history.

(56) References Cited

U.S. PATENT DOCUMENTS

| | | | |
|---|---|---|---|
| 6,431,172 | B1 | 8/2002 | Bordewick |
| 7,546,837 | B2 | 6/2009 | Busch |
| 8,100,125 | B2 | 1/2012 | Duquette |
| 8,297,285 | B2 * | 10/2012 | Henry ................... A61M 16/06 128/205.25 |
| 8,371,301 | B2 * | 2/2013 | Biener ................... A61M 16/06 128/205.25 |
| 8,770,190 | B2 * | 7/2014 | Doherty ............ A61M 16/0816 128/200.24 |
| 8,851,075 | B2 | 10/2014 | Ng |
| 9,162,034 | B2 * | 10/2015 | Veliss ................... A61M 16/06 |
| 9,168,346 | B2 | 10/2015 | Pierro |
| 9,180,269 | B2 * | 11/2015 | Dureus ................. A61M 16/06 |
| D799,699 | S * | 10/2017 | Higgins ....................... D24/164 |
| 2006/0207599 | A1 | 9/2006 | Busch et al. |
| 2007/0277828 | A1 | 12/2007 | Ho |
| 2008/0011305 | A1 | 1/2008 | Chandran et al. |
| 2008/0060649 | A1 | 3/2008 | Veliss |
| 2008/0264413 | A1 * | 10/2008 | Doherty ................. A61M 16/06 128/202.27 |
| 2008/0295846 | A1 | 12/2008 | Han |
| 2009/0183739 | A1 | 7/2009 | Wondka |
| 2010/0018534 | A1 | 1/2010 | Veliss |
| 2010/0282264 | A1 * | 11/2010 | Chang ................... A61M 16/06 128/206.21 |
| 2010/0307502 | A1 | 12/2010 | Rummery |
| 2011/0247619 | A1 * | 10/2011 | Formica ............ A61M 16/0875 128/204.18 |
| 2012/0073576 | A1 | 3/2012 | Wondka |
| 2012/0132210 | A1 | 5/2012 | Matula, Jr. |
| 2012/0204870 | A1 | 8/2012 | McAuley |
| 2012/0283592 | A1 | 11/2012 | Schuessler |
| 2013/0133664 | A1 * | 5/2013 | Startare ................. A61M 16/06 128/206.24 |

FOREIGN PATENT DOCUMENTS

| | | |
|---|---|---|
| CN | 101588833 A | 11/2009 |
| CN | 102711886 A | 10/2012 |
| EP | 0462412 A2 | 12/1991 |
| EP | 1057494 A2 | 12/2000 |

* cited by examiner

MANIFOLD ASSEMBLY FOR RESPIRATORY INTERFACE DEVICE

CROSS-REFERENCE TO RELATED APPLICATIONS

This patent application claims the priority benefit under 35 U.S.C. § 371 of international patent application no. PCT/IB2014/059250, filed Feb. 26, 2014, which claims the priority benefit under 35 U.S.C. § 119(e) of U.S. Provisional Application No. 61/773,992 filed on Mar. 7, 2013, the contents of which are herein incorporated by reference.

BACKGROUND OF THE INVENTION

1. Field of the Invention

The disclosed and claimed concept relates to respiratory interface devices for transporting a gas to and/or from an airway of a user, and, in particular, to a manifold assembly for a respiratory interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from a pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask component of the device in a tight enough seal against the patient's face without discomfort.

A number of known patient interface devices provide airflow to the patient through the headgear via one or more delivery conduits that warp around portions of the head as part of the headgear. That is, the headgear includes a tubing assembly with a manifold. The manifold is coupled to, and in fluid communication with, a delivery conduit. The delivery conduit is further coupled to, and in fluid communication with, the pressure/flow generating device. Such known patient interface devices, however, have a number of drawbacks.

For example, when a patient wearing a patient interface device moves, e.g. during sleep, forces that act on the delivery conduit are transferred to the manifold and on to the tubing assembly. As the tubes of the tubing assembly are in contact with the patient, and often in contact with the patient's face, any significant movement of the tubing assembly is likely to disturb the patient.

One construct structured to lessen the forces transferred to the patient incorporates rotational couplings at various locations, such as at the manifold. The rotational couplings allow the various conduits and tubes to rotate thereby absorbing the rotational forces. A rotational coupling, however, requires that the tube at the coupling between the manifold and the tubes be substantially circular. A manifold, as well as the tubes, with a circular cross section contacts the patient over a limited area. That is, only a small portion of a manifold coupling with a circular cross section contacts the patient. Such a limited area of contact concentrates stresses, such as, but not limited to, stress created by a lateral force action upon the manifold. Thus, while a manifold that includes rotational couplings with the delivery tubes absorbs rotational forces, such a configuration concentrates other forces.

Accordingly, a need exists for a manifold assembly that decouples portions of the manifold body from external forces applied to the delivery conduit. Further, a need exists for a manifold assembly that includes non-circular couplings to the delivery tubes that extend over the patient's head.

SUMMARY OF THE INVENTION

One embodiment of the presently disclosed concept provides a respiratory interface device includes a manifold assembly including a manifold body and a rotational coupling. The manifold body includes an elastic portion. The rotational coupling includes a rigid conduit. The rigid conduit is rotatably coupled to the manifold body elastic portion. In this configuration, the rotational coupling and the elastic portion decouple the remaining portions of the manifold body from external forces applied to the rigid conduit.

Another embodiment of the presently disclosed concept provides a manifold wherein the manifold openings, other than openings for the coupling with the delivery conduit, are non circular. That is, the manifold openings are couplings for the tubes of the tubing assembly. When the manifold openings are not substantially circular, the tubes at the manifold coupling locations are also not substantially circular. Thus, the manifold coupling and tubes may have a cross-sectional shape that reduces stress as compared to a circular manifold coupling and tube. Thus, it is the non-circular shape of the manifold opening that solves the stated problem.

It is a further object of this invention to provide a method of using a respiratory interface device wherein the respiratory interface device includes a manifold assembly including a manifold body and a rotational coupling, the manifold body including an elastic portion, the rotational coupling including a rigid conduit, the rigid conduit rotatably coupled to the manifold body elastic portion; and wherein the rotational coupling and the elastic portion decouple the remaining portions of the manifold body from external forces applied to the rigid conduit, the method including the steps of: applying a force to the rigid conduit, and, allowing the rotational coupling and the elastic portion to absorb the force so that the remaining portions of the manifold body are substantially unaffected by the force.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 10A shows the elastic portion subjected to an upward force applied along the Z-axis. FIG. 10B shows an unbiased elastic portion. FIG. 10C shows the elastic portion subjected to a downward force applied along the Z-axis;

FIG. 11A shows the elastic portion subjected to a leftward force applied along the X-axis. FIG. 11B shows an unbiased elastic portion. FIG. 11C shows the elastic portion subjected to a rightward force applied along the X-axis;

FIG. 12A shows the elastic portion subjected to a leftward force applied in a direction parallel to, but spaced from, the X-axis; this force generates a rotational force about the Y-axis. FIG. 11B shows an unbiased elastic portion. FIG. 11C shows the elastic portion subjected to a rightward force applied in a direction parallel to, but spaced from, the X-axis; this force generates a rotational force about the Y-axis;

FIG. 14A shows an unbiased manifold assembly. FIG. 14B shows a manifold assembly biased downwardly and to the left;

FIG. 15A is a side view of a stand-off device disposed on the rigid conduit body. FIG. 15B is a bottom view of a stand-off device disposed on the rigid conduit body;

DETAILED DESCRIPTION OF EXEMPLARY EMBODIMENTS

Figure 1:
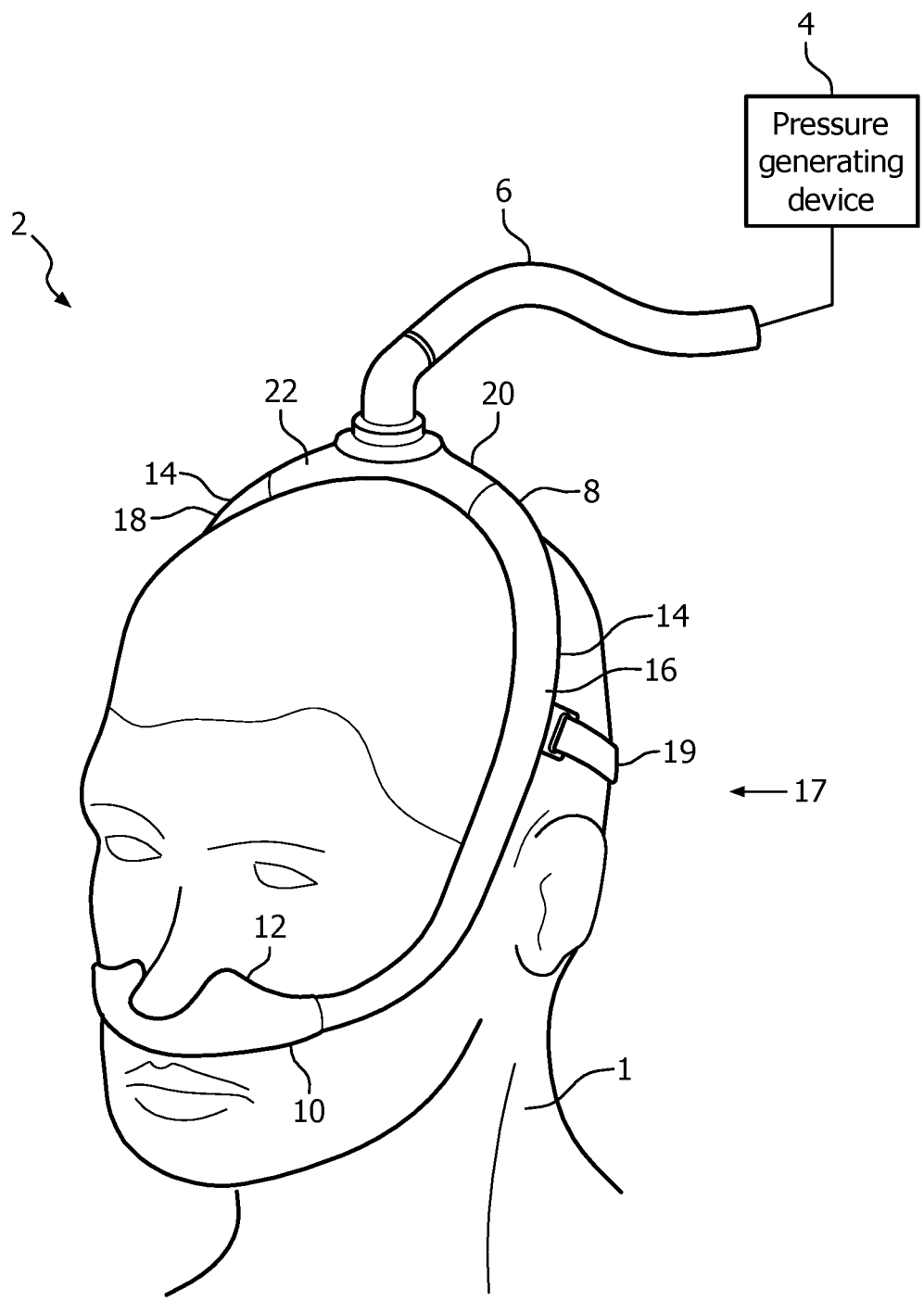
FIG. 1 is a schematic isometric view of a respiratory interface device.

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the statement that two or more parts or components "engage" one another shall means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

As used herein, "motion" and the forces and reaction forces associated therewith relate to forces created by a patient moving relative to a pressure generating device. Such motion occurs, in an exemplary embodiment, when a patient changes sleep positions. The motion of the patient causes hose drag, i.e. any forces generated by a delivery conduit moving such as, but not limited to, drag created by friction between the delivery conduit and bedding. Accordingly, it is understood that such "motion" is limited to movement between about 1 mm and 30 mm and which creates a force, or reaction force, of between about 0.1 newtons and 50 newtons.

As used herein, "absorbing" when used in the phrase "absorbing motion" or "absorbing forces" means that the forces and reaction forces created by patient motion are not significantly transferred to the patient.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As shown in FIG. 1, a respiratory interface device 2 is adapted to provide a regimen of respiratory therapy to a patient 1 according to one exemplary embodiment of the present invention. Respiratory interface device 2 includes a pressure generating device 4, a delivery conduit 6 fluidly coupled to a tubing assembly 8, and a patient interface device 10 fluidly coupled to tubing assembly 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 10 through tubing assembly 8 (the breathing gas enters at the top of the head of patient 1). Delivery conduit 6, tubing assembly 8 and patient interface device 10 are often collectively referred to as a patient circuit.

Patient interface device 10 includes a patient sealing element 12. In an exemplary embodiment, patient sealing element 12 is a nasal cushion made of a soft, flexible material, such as, without limitation, silicone, an appropriately soft thermoplastic elastomer, a closed cell foam, or any combination of such materials. However, any type of patient sealing element, such as a nasal/oral mask, a nasal pillow or a full face mask, which facilitates the delivery of the flow of breathing gas to the airway of a patient, may be used as sealing element 12 while remaining within the scope of the present invention.

Tubing assembly 8 includes a number of tubular members 14 as well as a manifold assembly 20. Each tubular member 14 includes a first end 13 and a second end 15. Each tubular member first end 13 is coupled to, and in fluid communication with, manifold 20 (as described below). Each tubular member second end 15 is coupled to, and in fluid communication with, patient interface device 10.

Manifold assembly 20 is disposed at the top of the head of patient 1 and tubular members 14 extend from manifold assembly 20 to sealing element 12. In an exemplary embodiment, there are two tubular members 14, namely left and right side arms 16, 18. Tubular members 14, have a non-circular cross-section. That is, each tubular member 14 is not substantially circular. In one embodiment, each tubular member 14 has a generally D-shaped cross-section wherein the generally flat side is disposed adjacent the user's head. As shown, tubular members 14, i.e. left and right side arms 16, 18, encircle, or partially encircle, the head of patient 1. Patient interface device 10 may further include a support assembly 17. As shown, support assembly 17 includes a rear strap 19 coupled to left and right side arms 16, 18 which also encircles, or partially encircles, the head of patient 1. That is, rear strap 19 is structured to engage the rear of the head of patient 1. In another embodiment, not shown, tubing assembly 8 includes single tubular member 14 that extends centrally, i.e. from manifold assembly 20 generally over the patient's forehead and nose, to sealing element 12.

Figure 2:
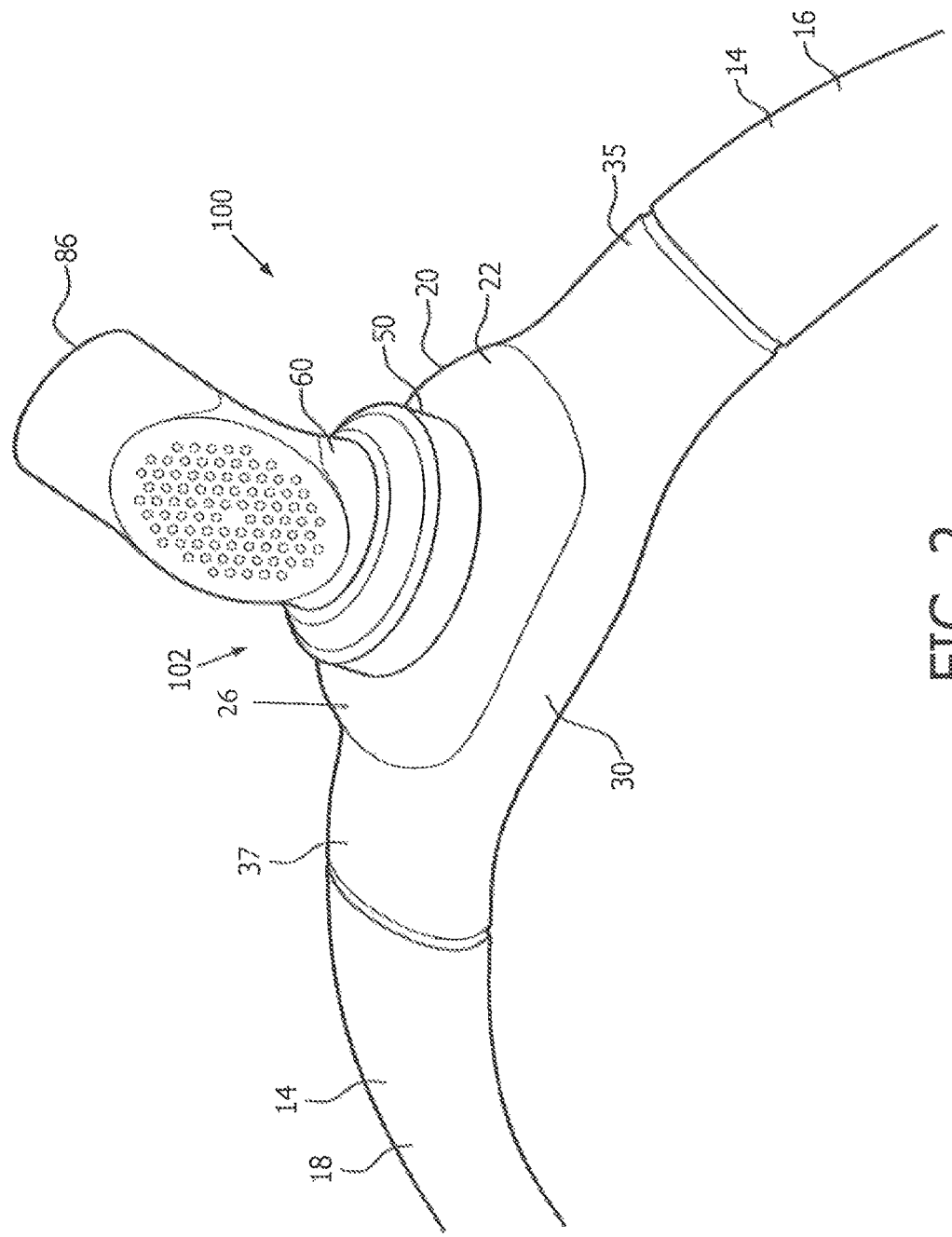
FIG. 2 is an isometric view of a manifold assembly.
Figure 3:
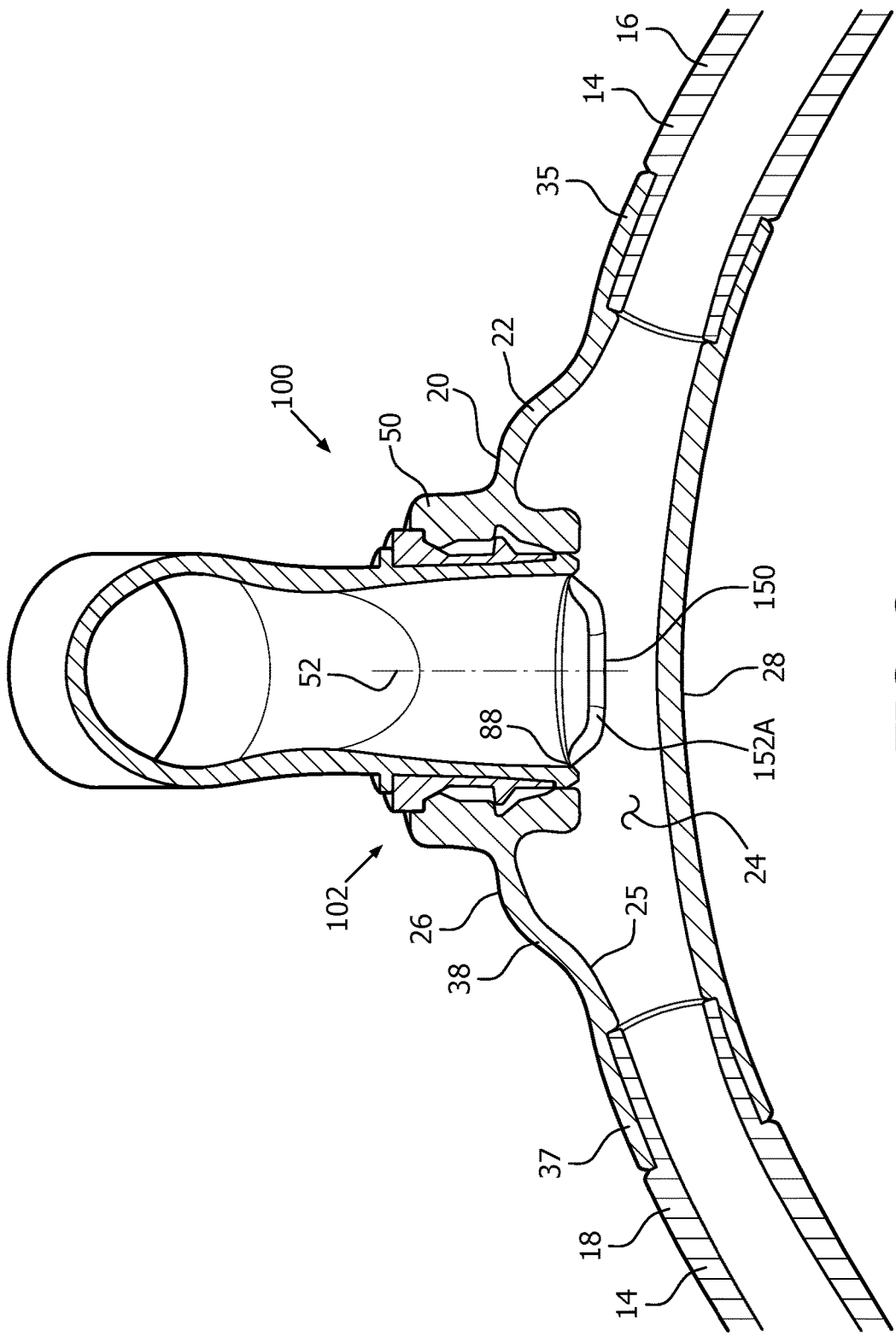
FIG. 3 is a front cross-sectional view of a manifold assembly.
Figure 4:
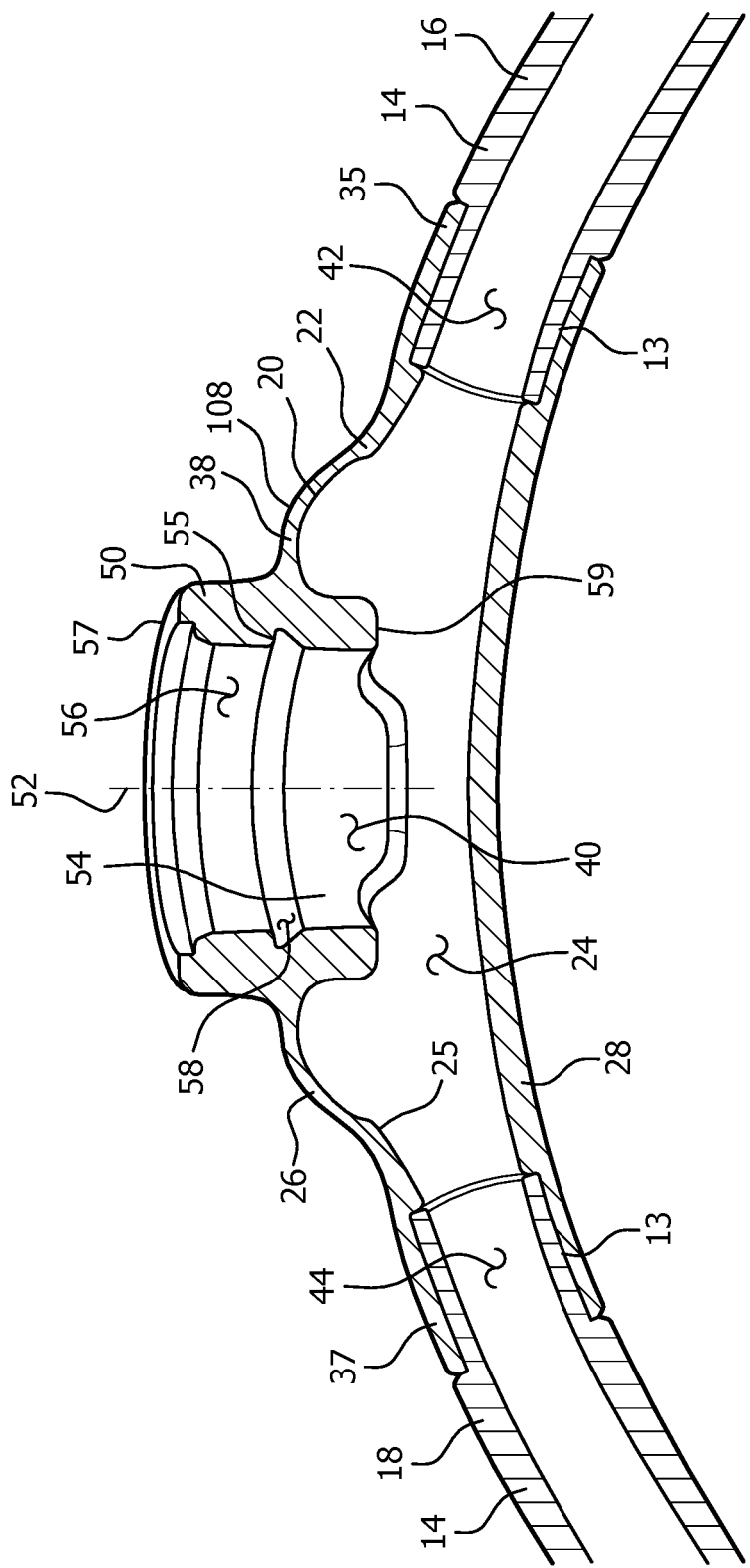
FIG. 4 is a front cross-sectional view of a manifold assembly body.
Figure 5:
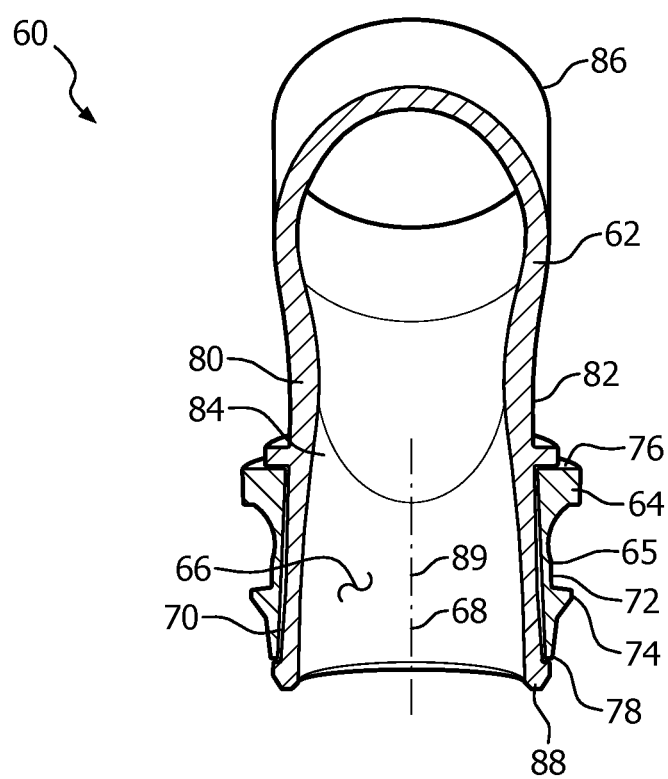
FIG. 5 is a front cross-sectional view of a conduit assembly.
Figure 6:
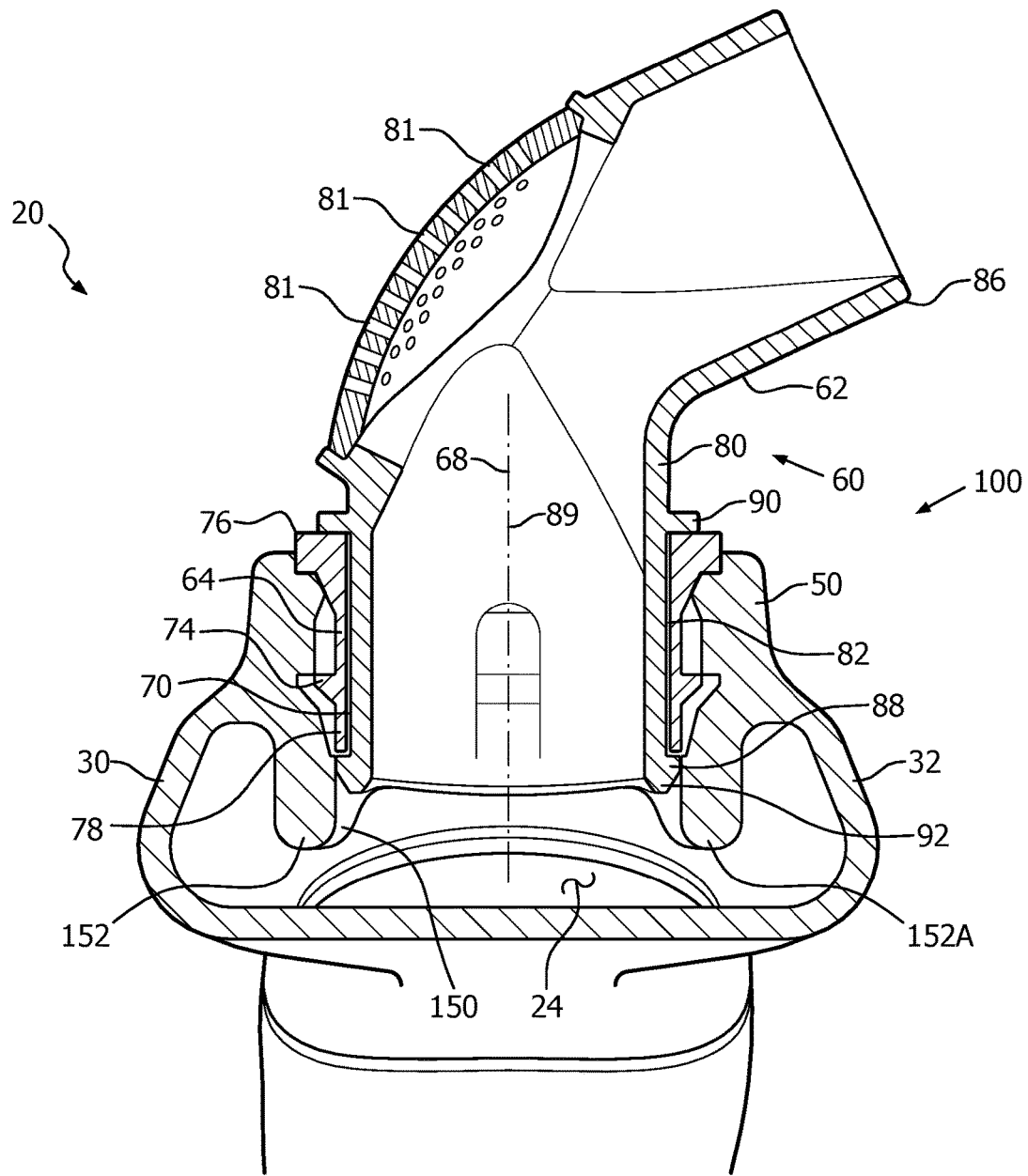
FIG. 6 is a side cross-sectional view of a manifold assembly.
Figure 7:
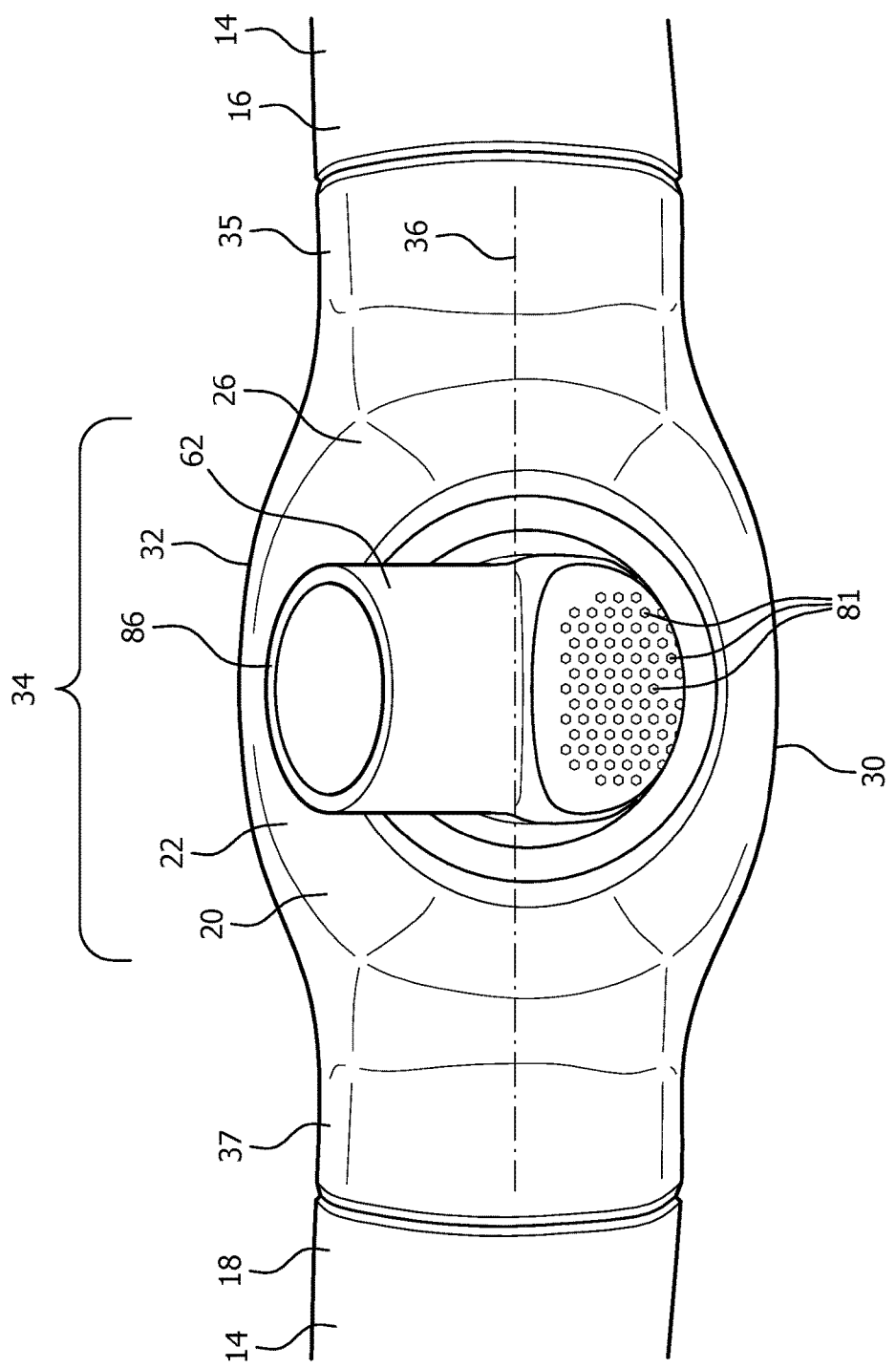
FIG. 7 is a top view of a manifold assembly.

As shown in FIGS. 2-4, manifold assembly 20 includes a generally hollow manifold body 22 and a rotational coupling 100. Rotational coupling 100 includes at least two components; a first opening 40 (FIG. 4) on manifold body 22 and a conduit assembly 60 (FIG. 5). First opening 40 and conduit assembly 60 are discussed in detail below. Manifold body 22 defines a generally enclosed space 24 (FIG. 4). Thus, manifold body 22 includes an inner surface 25 (FIG. 4). In an exemplary embodiment, manifold body 22 is a tubular body with a generally D-shaped cross-section, see FIG. 6. As with tubular members 14, the generally flat side is disposed adjacent the user's head. Further, in an exemplary embodiment, manifold body 22 includes an upper wall 26, a lower wall 28, a first sidewall 30 (FIG. 6) and a second sidewall 32 (FIG. 6). In an exemplary embodiment, and as shown in FIG. 7, manifold body 22 includes a medial portion 34 that has an increased cross-sectional area. Further, manifold body upper wall 26 at medial portion 34, in an exemplary embodiment, is generally planar and generally parallel to manifold body lower wall 28 at medial portion 34. Manifold body lower wall 28 may have an increased thickness at medial portion 34. As described below, various embodiments of a stand-off device 150 include protrusions 152 that are structured to engage manifold body lower wall 28. The increased thickness of manifold body lower wall 28 absorbs or dissipates the force applied to manifold body lower wall 28 so that the force transferred to the head of the patient 1 are limited.

As shown, in an exemplary embodiment, manifold body 22 is elongated with a longitudinal axis 36 (FIG. 7) that extends generally laterally. That is, manifold body longitudinal axis 36 extends in a direction parallel to a line extending between the patient's ears. In this configuration, manifold body 22 includes a left, first lateral end 35 and a right, second lateral end 37. As described below, left and right side arms 16, 18 can be coupled to manifold body 22 while extending about the left and right side of the head of patient 1.

Manifold body 22 is constructed of a soft, flexible material such as, but not limited to, silicone rubber. In an exemplary embodiment, manifold body 22 has a hardness of between about 3 shore A and 85 shore A, or between about 20 shore A and 70 shore A or about 60 shore A. Further, upper wall 26 at medial portion 34 is structured to be more flexible than the other portions of manifold body 22. As such, upper wall 26 at medial portion 34 is also identified as "elastic portion 38." Elastic portion 38 is described in more detail below.

In an exemplary embodiment, shown in FIG. 4, wherein tubing assembly 8 includes two tubular members 14, manifold body 22 includes a first opening 40, a second opening 42, and a third opening 44. As noted above, in this embodiment, manifold body longitudinal axis 36 extends in a direction parallel to a line extending between the patient's ears. Further, in this configuration, second opening 42 and third opening 44 are disposed on manifold body lateral ends 35, 37. Second opening 42 and third opening 44 are not substantially circular. As shown, in one embodiment, second opening 42 and third opening 44 have a D-shaped cross-sectional shape corresponding to tubular members 14. In this configuration, left and right side arms 16, 18 can be selectively coupled to, and in fluid communication with, second opening 42 and third opening 44, respectively. Further, the generally planar portion of the D-shaped second opening 42 and third opening 44 is disposed adjacent the head of the patient 1.

That is, tubular members 14, and more specifically tubular member first ends 13, are coupled to, and in fluid communication with, second opening 42 and third opening 44, respectively. In the embodiment shown, tubular members 14, and more specifically tubular member first ends 13, are inserted into second opening 42 and third opening 44. For example, manifold body 22 can form a nozzle (not shown) about second opening 42 and a tubular member 14, and more specifically a tubular member first end 13, can be disposed over the nozzle. It is noted that, because second opening 42 and third opening 44 have a D-shaped cross-sectional shape, left and right side arms 16, 18 cannot rotate at the interface between manifold body 22 and the left and right side arms 16, 18. It is further noted, however, that manifold body 22 at D-shaped second opening 42 and third opening 44 may lay comfortably against the head of the patient 1.

First opening 40 is disposed on elastic portion 38. First opening 40 is also part of rotational coupling 100. Manifold body 22 at first opening 40 may have an increased thickness thereby defining a collar 50. Collar 50, shown in FIG. 4, and in an exemplary embodiment, extends above and below upper wall 26. That is, collar 50 extends into enclosed space 24 as well as outwardly from upper wall 26. In an exemplary embodiment, collar 50 is substantially circular and includes an axis 52. Collar 50 includes a substantially circular inner surface 54 that extends generally parallel to collar axis 52. That is, collar 50 defines a substantially circular passage 56. Collar inner surface 54 includes a latching groove 58. Latching groove 58 is a groove wherein the outer surface 55, i.e. the surface disposed furthest from enclosed space 24, is a planar surface extending in a plane that is generally normal to collar axis 52.

Collar 50 is, in one embodiment (not shown), one component of rotational coupling 100. That is, a component, such as, but not limited to, rigid member 62, contacts collar 50 and rotates therein. As described below, in another exemplary embodiment, collar 50 is structured to have a hub 64 disposed therein. In this embodiment, hub 64 defines a substantially circular inner surface 70. In this embodiment, because hub 64 defines a substantially circular inner surface 70, collar 50 does not have to define a substantially circular inner surface 70. That is, in another exemplary embodiment (not shown) collar 50 defines a non-circular cross-sectional shape. In this embodiment, the cross-sectional shape of hub 64 corresponds to the cross-sectional shape of collar 50.

In the exemplary embodiment, however, collar 50 includes a substantially circular inner surface 54 and conduit assembly 60 has a corresponding cross-sectional shape. That is, conduit assembly 60, shown in FIG. 5, includes a rigid conduit 62 and a hub 64. Hub 64 includes a body 65 that defines a substantially circular passage 66. That is, hub body 65 includes an axis 68 and a radial inner surface 70. Hub body inner surface 70 extends substantially parallel to hub body axis 68. That is, hub body inner surface 70 is substantially circular. Hub body axis 68 is also the hub axis of rotation. Further, hub body axis 68 is also the axis of rotation for rotational coupling 100. Hub body 65 has a length. Hub body 65 further includes an outer surface 72. In the exemplary embodiment shown, hub body outer surface 72 is a radial, i.e. circular, surface. Hub body outer surface 72 includes a latching tongue 74. Latching tongue 74 corresponds to latching groove 58. In another exemplary embodiment, latching tongue 74 snuggly corresponds to latching groove 58. That is, the cross-sectional area of latching groove 58 is slightly smaller than the cross-sectional area of latching tongue 74. Thus, collar 50, which is made from a soft, flexible material, must stretch when latching tongue 74 is disposed in latching groove 58. In the exemplary embodiment shown, hub outer surface 72 is generally circular. As noted above, hub outer surface 72 is not limited to a generally circular cross-section shape. Hub body 65 further includes an outer, first end 76 and an inner, second end 78. When assembled, as described below, hub body first end 76 is disposed outside of enclosed space 24, and, hub body second end 78 is disposed inside of enclosed space 24.

Rigid conduit 62 includes an elongated tubular body 80. Rigid conduit body 80 selectively includes a number of vent openings 81. Rigid conduit body 80 includes a radial outer surface 82, an inner surface 84, an outer, first end 86 and an inner, second end 88. That is, rigid conduit body outer surface 82 is substantially circular. Rigid conduit body 80 further includes an axis 89. Rigid conduit body 80 selectively is an angled body. That is, in the exemplary embodiment shown, conduit body first end 86 is disposed at an angle relative to conduit body second end 88. In an exemplary embodiment, the angle of conduit body first end 86 relative to conduit body second end 88 is between about 0 degrees (i.e. a generally straight conduit) and 120 degrees (i.e. a conduit with an acute bend), or, between about 50 degrees (i.e. a conduit with an obtuse bend) and 90 degrees (i.e. a conduit with a right angle).

As shown in FIG. 6, in an exemplary embodiment, the angle of conduit body first end 86 relative to conduit body second end 88 is about 60 degrees. At conduit body second end 88, rigid conduit body outer surface 82 extends substantially parallel to rigid conduit body axis 68. The axis of rotation for rigid conduit 62 is about rigid conduit body axis 89 at conduit body second end 88. Accordingly, as used herein, unless otherwise noted, "rigid conduit body axis 89" means rigid conduit body axis 89 at conduit body second end 88. Rigid conduit body axis 89 is generally, or substantially, aligned with hub body axis 68, when conduit body 80 is disposed in hub body 65. As shown, rigid conduit body inner surface 84, at conduit body second end 88, is generally circular, but may have other cross-sectional shapes as well. When assembled, as described below, rigid conduit first end 86 is disposed outside of enclosed space 24, and, rigid conduit body second end 88 is disposed inside of enclosed space 24. Rigid conduit body 80 includes a first radial flange 90. Rigid conduit body second end 88 includes a second radial flange 92. Rigid conduit first radial flange 90 is disposed on the medial portion of rigid conduit body 80 below the angle (if present). The location of rigid conduit first radial flange 90 is determined by the height of hub body 65, noted above, and the location of rigid conduit second radial flange 92. That is, the axial spacing between rigid conduit first radial flange 90 and rigid conduit second radial flange 92 is corresponds to the length of hub body 65.

In this configuration, rigid conduit 62 and hub 64 are structured to be coupled as a rotational coupling. That is, the outer diameter of rigid conduit body outer surface 82 corresponds to the hub body inner surface 70. In another embodiment, the outer diameter of rigid conduit body outer surface 82 substantially corresponds to the hub body inner surface 70. Thus, rigid conduit 62 is rotatably disposed within hub 64. When rigid conduit 62 is disposed within hub 64, hub body axis 68 and rigid conduit body axis 89 are substantially aligned. Further, when rigid conduit 62 is disposed within hub 64, rigid conduit first radial flange 90 is disposed immediately adjacent hub body first end 76, and, rigid conduit second radial flange 92 is disposed immediately adjacent hub body second end 78. In another embodiment, when rigid conduit 62 is disposed within hub 64, rigid conduit first radial flange 90 engages adjacent hub body first end 76, and, rigid conduit second radial flange 92 engages hub body second end 78. Thus, in this configuration, rigid conduit 62 is rotatably coupled to hub 64 and rotates about rigid conduit body axis 89.

Hub 64 is coupled, and in an exemplary embodiment fixed, to manifold body 22 at first opening 40. That is, hub 64 is disposed within collar passage 56. When hub 64 is disposed within collar passage 56, hub latching tongue 74 is disposed within latching groove 58. Thus, rigid conduit 62 is rotatably coupled to hub 64 and hub 64 is fixed to manifold body 22. In this configuration, rigid conduit 62 is rotatably coupled to manifold body 22. That is, the combination of rigid conduit 62 and hub 64 form rotational coupling 100. As used herein, a "rotational coupling" includes at least two elements coupled in a manner so that one element can rotate relative to the other element. As noted above, in another embodiment, not shown, first opening 40, or more specifically collar 50, defines a substantially circular passage 56 and rigid conduit 62 is rotatably disposed in first opening 40. That is, in another embodiment (not shown) there is no hub and rigid conduit 62 is directly and rotatably coupled to first opening 40. Thus, in the other embodiment (not shown) rigid conduit 62 and first opening 40 form rotational coupling 100.

As noted above, first opening 40 is disposed on elastic portion 38. Elastic portion 38 is structured to be more flexible than the other portions of manifold body 22. Making elastic portion 38 more flexible than the other portions of manifold body 22 may be accomplished in several different ways. In one exemplary embodiment, elastic portion 38 is generally planar but the material forming elastic portion 38 is generally thinner than the remaining portions of the manifold body 22. In another exemplary embodiment, elastic portion 38 is made from a material that is softer than the remaining portions of manifold body 22. In an exemplary embodiment, when manifold body 22 has a hardness of about 60 shore A, elastic portion 38 is made from material having a hardness of about 10 shore A. It is understood that, if the manifold body 22 is softer then about 60 shore A, then elastic portion 38 is made from material that is softer than manifold body 22, Accordingly, as used herein, a "resilient member" is a portion of manifold body 22 that is either thinner or has a hardness that is less than the hardness of the remaining portions of manifold body 22.

Figure 8:
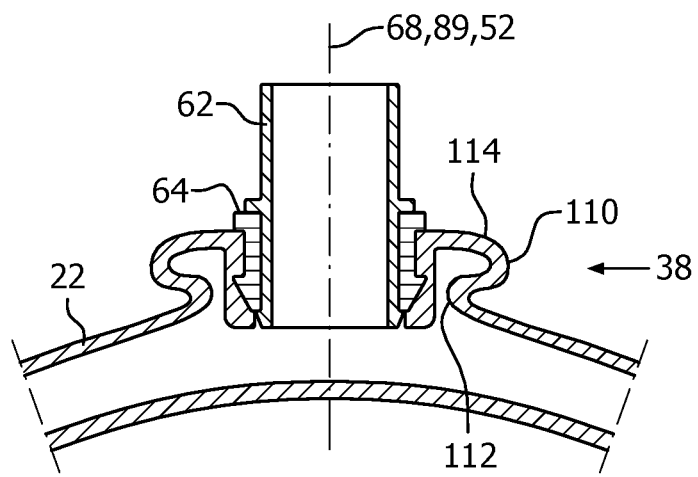
FIG. 8 is a cross-sectional view of an elastic portion with a bellows.

That is, as shown in FIG. 4, elastic portion 38 is a resilient member 108. In another exemplary embodiment, shown in FIG. 8, elastic portion 38 includes a bellows 110. Bellows 110 is incorporated into elastic portion 38 wherein elastic portion 38 doubles back on itself in a direction generally normal to rigid conduit body axis 89. That is, elastic portion 38 includes a first horizontally curved portion 112, wherein first horizontally curved portion 112 curves away from rigid conduit body axis 89, and a second horizontally curved portion 114, wherein second horizontally curved portion 114 curves toward rigid conduit body axis 89. In an exemplary embodiment bellows 110 extend away from enclosed space 24. In another exemplary embodiment, not shown, bellows 110 extend into enclosed space 24. Further, bellows 110, in an exemplary embodiment, not shown, includes more than one fold, i.e. more than two curved portions 112, 114.

Figure 9:
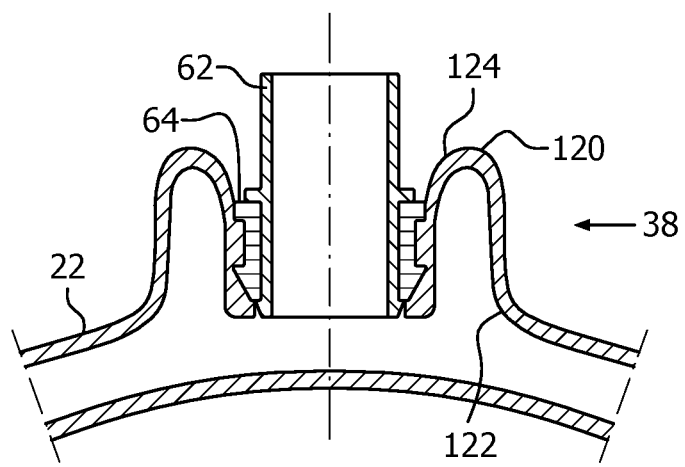
FIG. 9 is a cross-sectional view of an elastic portion with a rolling diaphragm.

In another embodiment, shown in FIG. 9, elastic portion 38 includes a rolling diaphragm 120. Rolling diaphragm 120 is incorporated into elastic portion 38 wherein elastic portion 38 doubles back on itself in a direction generally parallel to rigid conduit body axis 89. That is, elastic portion 38 includes a first vertically curved portion 122, wherein first vertically curved portion 122 curves away from enclosed space 24, and a second vertically curved portion 124, wherein second vertically curved portion 124 curves toward enclosed space 24. In an exemplary embodiment, rolling diaphragm 120 extends upwardly away from enclosed space 24. In another exemplary embodiment, not shown, rolling diaphragm 120 extends downwardly into enclosed space 24. Further, rolling diaphragm 120, in an exemplary embodiment, not shown, includes more than one fold, i.e. more than two curved portions 122, 124.

Thus, elastic portion 38 is structured to be distorted, i.e. stretched and/or compressed, as described below. It is understood that different areas of elastic portion 38 may be distorted differently as a result of a single force being applied. For example, and as described in detail below, a force acting laterally (along the X-axis as described below) will cause one side of elastic portion 38 to be stretched and the other side to be compressed. Other forces, however, may cause a generally uniform distortion of elastic portion 38. For example, an upward force, as shown in the Figures (along the Z-axis as described below) will stretch all areas of elastic portion 38.

When rotational coupling 100 is disposed on elastic portion 38, rotational coupling 100 and elastic portion 38 decouple the remaining portions of manifold body 22 from external forces applied to rigid conduit 62. That is, as used herein, "the remaining portions of manifold body" means the portions of manifold body 22 other than elastic portion 38. Further, "decouple . . . from external forces applied to rigid conduit" means that forces that act upon rigid conduit 62 are not significantly transferred to, i.e. act upon the, remaining portions of manifold body 22. Thus, rotational coupling 100 and elastic portion 38 form a "motion decoupling assembly" 102 that decouples the remaining portions of manifold body 22 from external forces applied to rigid conduit 62. More specifically, rotational coupling 100 and elastic portion 38 form a "multi-axis motion decoupling assembly" 102. As used herein, a "multi-axis motion decoupling assembly" is an assembly that absorbs linear motion along, and rotational motion about, the three axes of a Cartesian coordinate axis system. Further, as delivery conduit 6 is coupled, or directly coupled, to rigid conduit 62, any force applied to delivery conduit 6 is transferred to rigid conduit 62. As such, as used herein, a "force applied to rigid conduit 62" includes a force applied to delivery conduit 6. As noted in the definitions above, "motion" relates to motion of a patient 1 and to a limited range of motion. The limited range of motion creates a limited force acting on delivery conduit 6 and rigid conduit 62. It is understood that larger movements, and the forces created thereby, are absorbed by manifold body 22 as well as other elements such as, but not limited to, delivery conduit 6, while some forces are transferred to the head of patient 1. Thus, in one exemplary embodiment, patient 1 moves their head about 10 mm from an original position. In response to this motion, manifold body 22, and more specifically, elastic portion 38 stretches about 10 mm. Thus, the delivery conduit 6 does not move significantly and no significant force is transferred to patient 1. Further, manifold body 22 does not move significantly relative to the head of patient 1.

The following examples present various forces as described relative to a Cartesian coordinate system. It is understood that, when elastic portion 38 is generally circular, "one side" or "the side" of elastic portion 38, as used below, means generally a semicircular portion of elastic portion 38 wherein the dividing line between the "side" and the "other side" is generally a line similar to a diameter. It is understood that forces may act in combination, e.g. a linear and rotational force, or may act in a direction other than along or about a specific axis. When forces act in combination, or along/about a line other than an axis, the resulting effect on the rotational coupling 100 and the elastic portion 38 will be a combination of the motion or distortions described below.

Figure 10A:
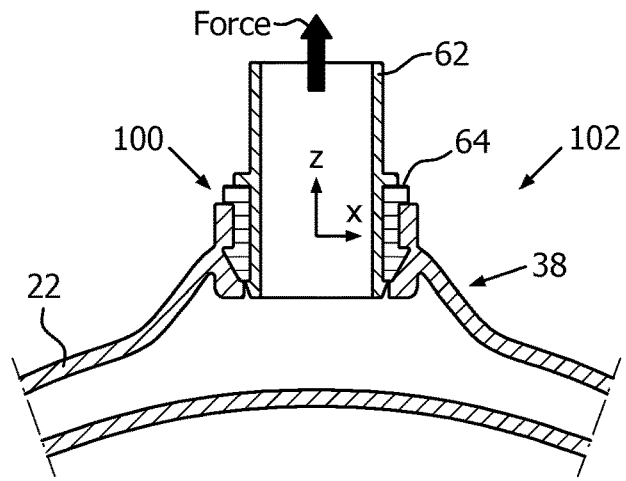
FIGS. 10A-10C are cross-sectional side views of a manifold assembly.
Figure 10B:
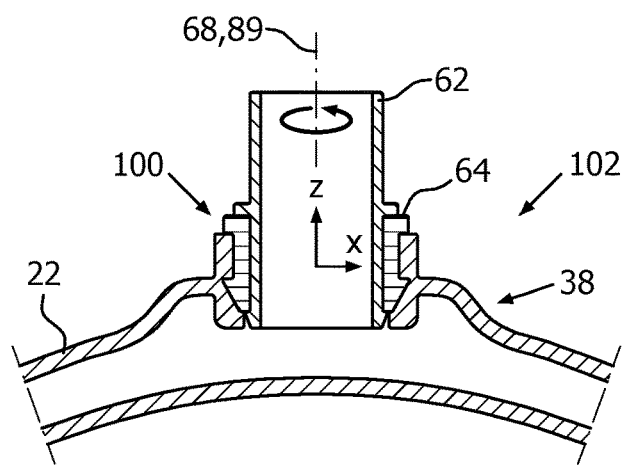
Figure 10C:
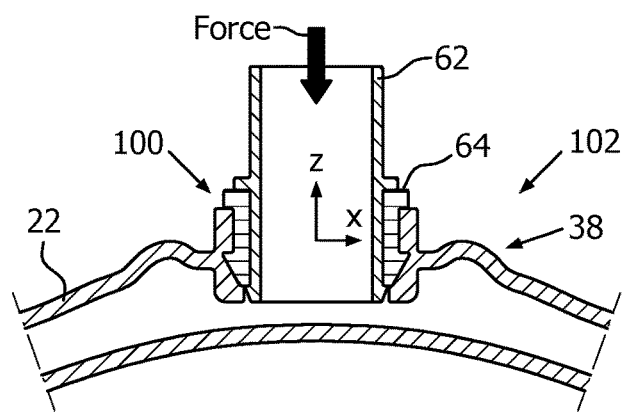

As shown in FIGS. 10A-10C, a Cartesian coordinate axis system is disposed with the Z-axis aligned with rigid conduit body axis 89. The X-axis extends laterally, i.e. generally parallel to a line extending between the patient's ears. The Y-axis, not shown, extends normal to the plane defined by the X-axis and the Z-axis, i.e. toward the viewer. In the exemplary embodiment, elastic portion 38 is generally planar and the origin of the coordinate axis system is disposed generally in the plane of elastic portion 38. Generally, forces in a Cartesian coordinate system may be expressed as either a linear force, such as, but not limited to, a force acting along an axis, or a rotational force, such as, but not limited to, a force acting about, i.e. twisting about, an axis. Further, as rigid conduit 62 is elongated and/or coupled to delivery conduit 6, a rotational force is commonly created about the X-axis or Y-axis by a linear force spaced from the origin, e.g. a force acting parallel to an axis but offset from the origin. Such a force can be created by a force applied to delivery conduit 6, for example. Each of these forces, as well as the mechanism for decoupling the force from the remaining portions of manifold body 22 are described below.

A rotational force about the Z-axis, as shown in FIG. 10B, is decoupled from the remaining portions of manifold body 22 by the rotational coupling 100. That is, a rotational force about the Z-axis that is applied to rigid conduit 62 causes rigid conduit 62 to rotate relative to hub 64. Thus, a rotational force about the Z-axis that is applied to rigid conduit 62 is decoupled from the remaining portions of manifold body 22 because rigid conduit 62 rotates relative to hub 64 which is fixed to the manifold body 22.

A linear force along the Z-axis and acting upon rigid conduit 62 causes elastic portion 38 to stretch or be compressed. That is, the elastic nature of elastic portion 38 allows elastic portion 38 to stretch (FIG. 10A) or be compressed (FIG. 10C) thereby absorbing the linear force along the Z-axis. Thus, a linear force along the Z-axis that is applied to rigid conduit 62 is decoupled from the remaining portions of manifold body 22 because rigid conduit 62 moves with the elastic portion 38 in a direction along the Z-axis.

Figure 11A:
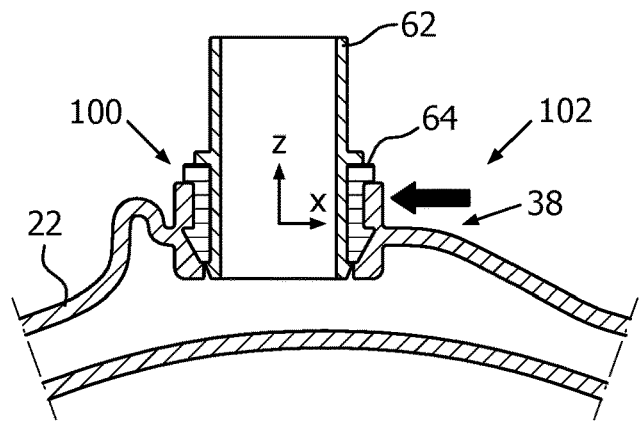
FIGS. 11A-11C are cross-sectional side views of a manifold assembly.
Figure 11B:
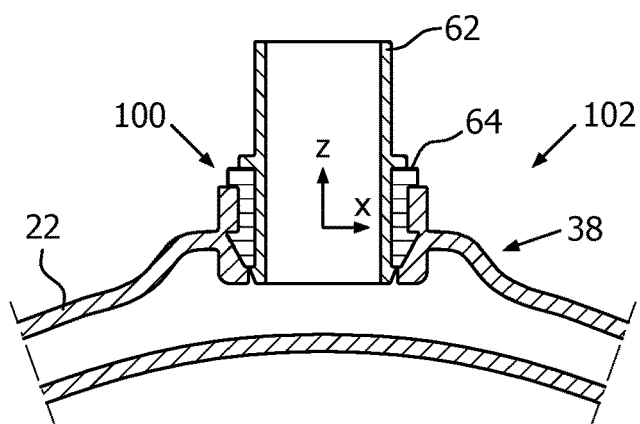
Figure 11C:
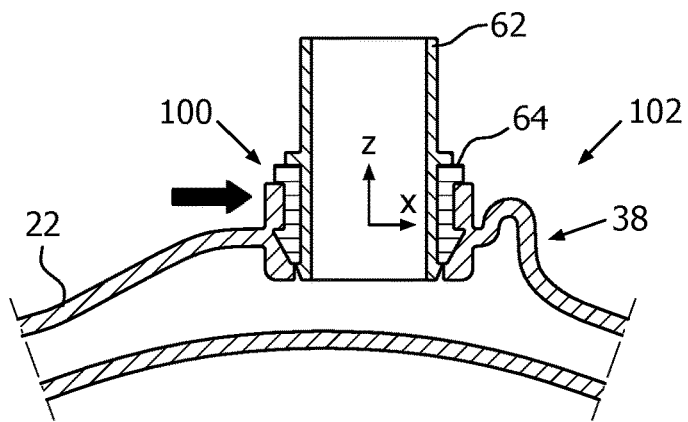

As shown in FIGS. 11A-11C, a linear force along the X-axis and acting upon rigid conduit 62 causes one side of elastic portion 38 to stretch and the opposing side of elastic portion 38 to be compressed. That is, a linear force along the X-axis and acting upon rigid conduit 62 causes the side of elastic portion 38 in the direction of the force to be compressed. For example, a linear force along the X-axis acting to the right, as shown in the figures, causes the right side of elastic portion 38 to be compressed. As is known, an elastic portion that is compressed may buckle as shown in the figures. Conversely, a linear force along the X-axis and acting upon rigid conduit 62 causes the side of elastic portion 38 opposite the direction of the force to be stretched. For example, a linear force along the X-axis acting to the right, as shown in the figures, causes the left side of elastic portion 38 to be stretched. It is understood that a linear force along the Y-axis and acting upon rigid conduit 62 causes one side of elastic portion 38 to stretch and the other side to compress, but with respect to the Y-axis rather than the X-axis.

Figure 12A:
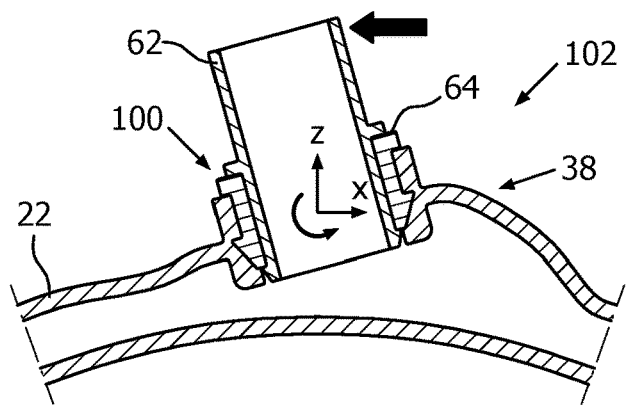
FIGS. 12A-12C are cross-sectional side views of a manifold assembly.
Figure 12B:
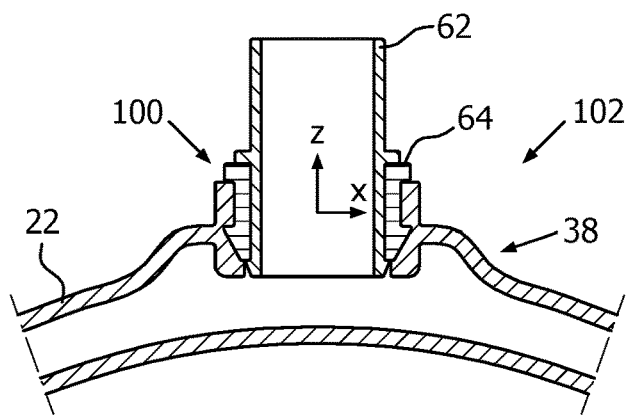
Figure 12C:
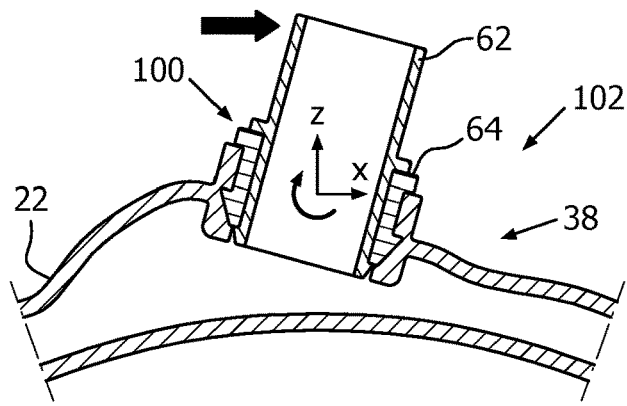

As shown in FIGS. 12A-12C, a rotational force about the Y-axis is created by a force acting upon rigid conduit 62 at a location that is spaced from the origin. Such a force causes one side of elastic portion 38 to stretch in the direction of the force and the opposing side of elastic portion 38 to stretch in a direction opposite the direction of the force. For example, as shown in FIG. 12A, a clockwise rotational force, as seen in the figures, about the Y-axis is created by a force biasing rigid conduit 62 to the right (as shown in the figure). Thus, the side of elastic portion 38 opposite the direction of the force (e.g. the left side when the force acting to the right) is stretched in the direction of the force (e.g., to the right) and the side of elastic portion 38 in the direction of the force (e.g. the right side when the force acting to the right) is stretched in a direction opposite the direction of the force (e.g. to the left).

Accordingly, the rotation of rotational coupling 100 and the deformation of elastic portion 38 effectively absorb forces applied to rigid conduit 62 and generated as a result of patient motion. Thus, the remaining portions of the manifold body 22 are substantially unaffected by a force applied to rigid conduit 62. It is again noted that forces will not typically act along or about a specific axis. When forces act in combination, i.e. along/about a line other than an axis, the resulting effect on the rotational coupling 100 and elastic portion 38 will be a combination of the motion or distortions described above. For example, a force acting in the X-Z plane from the right and at a 45 degree angle toward manifold body 22 will cause elastic portion 38 to deform, i.e. stretch, downwardly, as shown in FIG. 10C, as well as causing the left side of elastic portion 38 to compress, or stretch less, than the right side of elastic portion 38. It is understood that this is one example of a force not acting along or about an axis and this example is not limiting upon the claims.

As can be seen in FIG. 10C, a downward force acting along the Z-axis causes rigid conduit body second end 88, and more specifically second radial flange 92, to move toward manifold body lower wall 28. If conduit body second end 88 engages, or substantially engages, manifold body lower wall 28, the flow of gas through rigid conduit 62 may be reduced or cut off. Accordingly, an exemplary embodiment of manifold assembly 20 includes a stand-off device 150. Stand-off device 150, as shown in FIGS. 3 and 6, is structured to prevent conduit body second end 88 from engaging, or substantially engaging, manifold body lower wall 28. Stand-off device 150 may be part of collar 50, conduit body second end 88, or manifold body lower wall 28. That is, stand-off device 150 is disposed on manifold body inner surface 25 adjacent first opening 40 or, disposed on rigid conduit 62. Several embodiments (each described below) of stand-off device 150 include a number of protrusions 152 while other embodiments (each described below) include a "cage" 154. As used herein, a "cage" is a rigid structured with openings therethrough.

In an exemplary embodiment, shown in FIGS. 3 and 6, stand-off device 150 is disposed on collar 50. That is, collar 50 includes an outer, first end 57 and an inner, second end 59 (both in FIG. 4). Collar second end 59 is disposed within enclosed space 24. Collar second end 59 is also part of the manifold body inner surface 25. Collar second end 59 includes a number of protrusions 152A wherein protrusions 152A are spaced from each other. Protrusions 152A extend toward manifold body lower wall 28. Spaced protrusions 152A are also identified as "intermittent protrusions" 152A. As shown in FIG. 6, in an exemplary embodiment there are two protrusions 152A disposed on opposite sides of collar second end 59. In this configuration, and when a downward force acting along the Z-axis causes rigid conduit body second end 88, and more specifically second radial flange 92, to move toward manifold body lower wall 28, protrusions 152A will contact manifold body lower wall 28 and prevent rigid conduit body second end 88 from engaging manifold body lower wall 28. In this configuration, gas will flow in the space between protrusions 152A. It is noted that collar second end 59 is disposed adjacent first opening 40. That is, collar second end 59 and first opening 40 are near each other.

Figure 13:
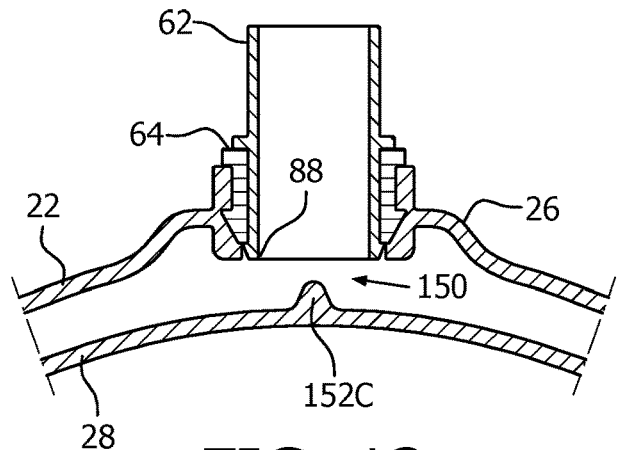
FIG. 13 is a cross-sectional front view of a manifold assembly with a stand-off device.

In another embodiment, shown in FIG. 13, stand-off device 150 is disposed on manifold body lower wall 28. That is, manifold body lower wall 28 includes a number of protrusions 152C wherein protrusions 152C are spaced from each other. Protrusions 152C extend toward manifold body upper wall 26. As shown in FIG. 13, in an exemplary embodiment, there is a single protrusion 152C disposed on manifold body lower wall 28. The single protrusion 152C is a ridge extending parallel to the Y-axis, as discussed above. The protrusion 152C extends substantially across manifold body lower wall 28. Thus, if rigid conduit 62 shifts relative to its original configuration, as shown in FIG. 13, protrusion 152C will still be disposed below some portion of rigid conduit body second end 88. In another embodiment, not shown, there are two protrusions 152C, each being ridges, disposed at about a right angle. In this configuration, and when a downward force acting along the Z-axis causes rigid conduit body second end 88, and more specifically second radial flange 92, to move toward manifold body lower wall 28, protrusions 152C will contact rigid conduit body second end 88 and prevent the entire perimeter of rigid conduit body second end 88 from engaging manifold body lower wall 28. In this configuration, gas will flow in the space between protrusions 152C or through the gap between rigid conduit body second end 88 and manifold body lower wall 28. It is noted that manifold body lower wall 28 is disposed adjacent first opening 40. That is, there are no elements between manifold body lower wall 28 and first opening 40.

Figure 14A:
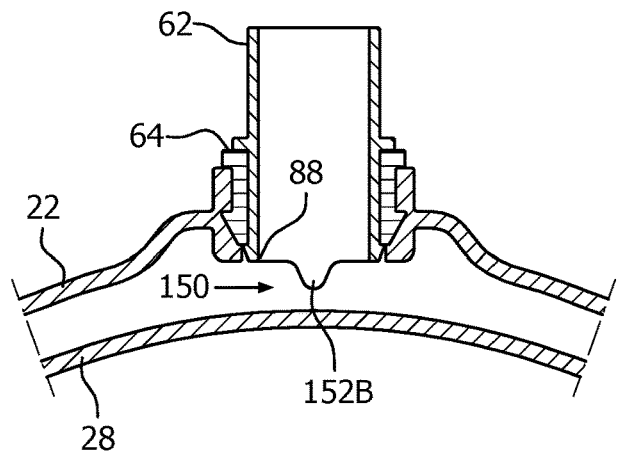
FIGS. 14A and 14B are cross-sectional front views of a manifold assembly with a stand-off device on the rigid conduit body.
Figure 14B:
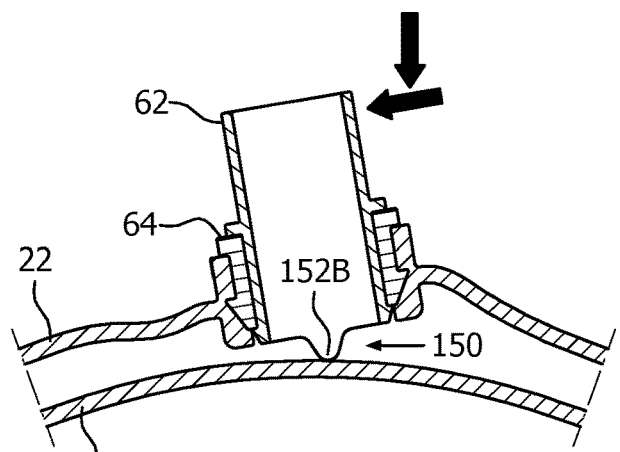

In another embodiment, shown in FIGS. 14A-14B, stand-off device 150 is disposed on rigid conduit body second end 88. That is, rigid conduit body second end 88, and more specifically second radial flange 92, includes a number of protrusions 152B wherein protrusions 152B are spaced from each other. Protrusions 152B extend toward manifold body lower wall 28. In an exemplary embodiment, there are two protrusions 152B disposed on opposite sides of rigid conduit body second end 88. In this configuration, and when a downward force acting along the Z-axis causes rigid conduit body second end 88, and more specifically second radial flange 92, to move toward manifold body lower wall 28, protrusions 152B will contact manifold body lower wall 28 and prevent the entire perimeter of rigid conduit body second end 88 from engaging manifold body lower wall 28. In this configuration, gas will flow in the space between protrusions 152B. It is noted that rigid conduit body second end 88 is disposed adjacent first opening 40. That is, rigid conduit body second end 88 and first opening 40 are near each other.

Figure 15A:
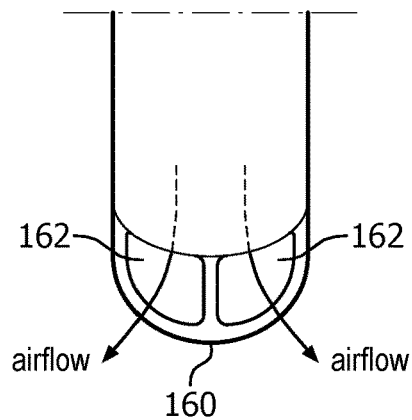
FIGS. 15A and 15B are views of a stand-off device disposed on the rigid conduit body.
Figure 15B:
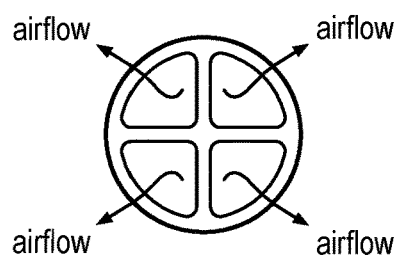
Figure 16:
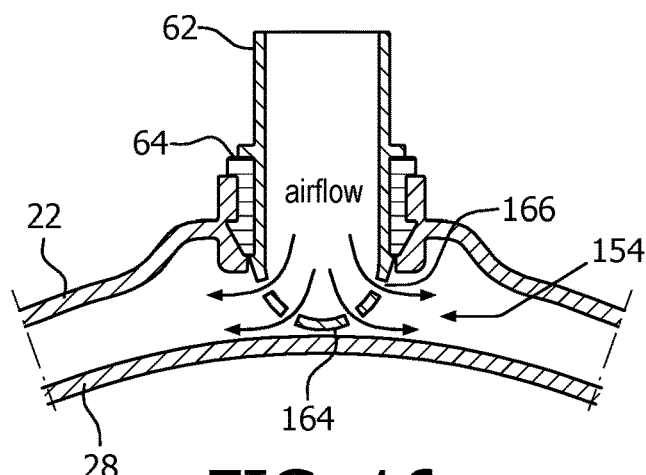
FIG. 16 is a cross-sectional side view of another embodiment of a stand-off device disposed on the rigid conduit body.
Figure 17:
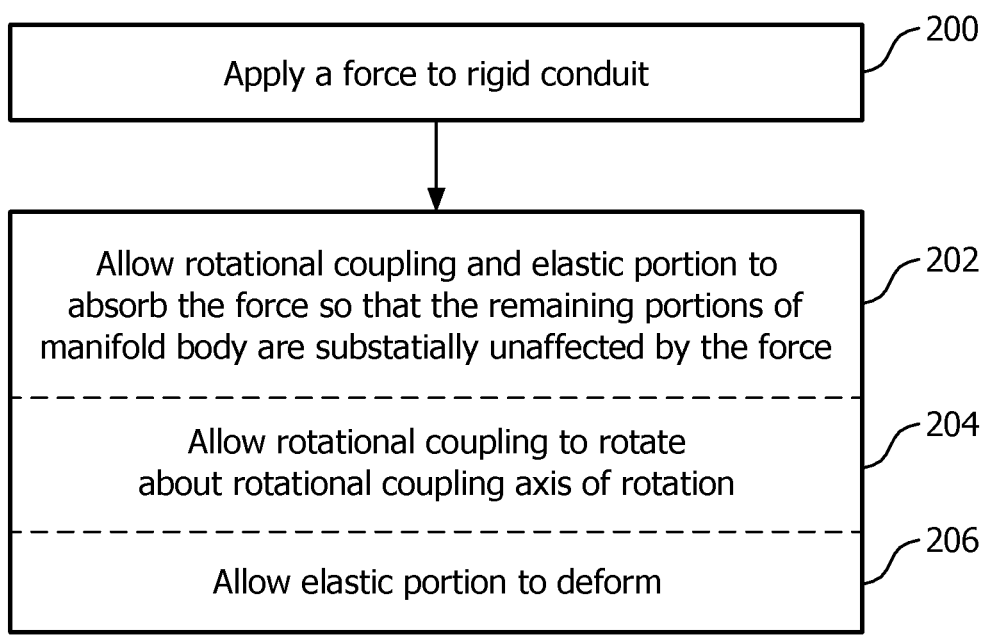
FIG. 17 is a flow chart of the steps associated with using the manifold assembly.

In another embodiment, shown in FIGS. 15A, 15B, and 16, stand-off device 150 is again disposed on rigid conduit body second end 88, but is in the form of cage 154. As used herein, a "cage" is a number of members defining a perimeter wherein the perimeter includes a number of openings therethrough. In one embodiment, as shown in FIGS. 15A and 15B, rigid conduit body second end cage 154 includes a number of thin, elongated, curvilinear members 160 wherein curvilinear members 160 are spaced from each other. That is, there are a number of stand-off member openings 162 between the members 160. In this embodiment, curvilinear members 160 define a perimeter. In another embodiment, shown in FIG. 16, cage 154 includes a generally hemispherical member 164 includes a number of openings 166 therethrough. In this embodiment, hemispherical member 164 defines a perimeter.

The method of using respiratory interface device 2 including manifold assembly 20, as described above, includes the following steps. A patient 1 applies 200 a force to rigid conduit 62, and, allows 202 rotational coupling 100 and elastic portion 36 to absorb the force so that remaining portions of manifold body 22 are substantially unaffected by the force. The step of allowing 202 rotational coupling 100 and elastic portion 36 to absorb the force so that remaining portions of manifold body 22 are substantially unaffected by the force includes the steps of allowing 204 rotational coupling 100 to rotate about rotational coupling axis of rotation, and, allowing 206 elastic portion 38 to deform.

In the claims, any reference signs placed between parentheses shall not be construed as limiting the claim. The word "comprising" or "including" does not exclude the presence of elements or steps other than those listed in a claim. In a device claim, "enumerating several" means, several of these means may be embodied by one and the same item of hardware. The word "a" or "an" preceding an element does not exclude the presence of a plurality of such elements. In any device claim, "enumerating several" means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A manifold assembly for a patient interface device, the manifold assembly comprising:
    a manifold body including an elastic portion wherein the elastic portion is more flexible than the other portions of manifold body;
    a rotational coupling including a rigid conduit, wherein the rigid conduit is rotatably coupled to the manifold body elastic portion, wherein the rotational coupling and the elastic portion form a motion decoupling assembly, and wherein the motion decoupling assembly decouples the remaining portions of the manifold body from external forces applied to the rigid conduit;
    wherein the manifold body is elongated and defines a generally enclosed space, the manifold body includes an upper wall;
    wherein the elastic portion is disposed on the upper wall;
    wherein the manifold body further includes a first opening and a second opening;
    wherein the first opening is disposed on the elastic portion of the upper wall;

wherein the rigid conduit includes a substantially circular cross-section; and
wherein the rigid conduit is rotatably coupled to the first opening.

2. The manifold assembly of claim 1, wherein:
the rotational coupling includes a conduit assembly;
the conduit assembly includes a hub;
the hub includes an axis of rotation, an outer radial surface and a radial inner surface;
the hub inner surface is substantially circular;
the rigid conduit includes a substantially circular outer surface;
the rigid conduit outer surface corresponds to the hub inner surface;
the hub is fixed to a medial portion of the upper wall; and
the rigid conduit is rotatably coupled to the hub.

3. The manifold assembly of claim 2, wherein the first opening snuggly corresponds to the hub outer radial surface.

4. The manifold assembly of claim 1, wherein the elastic portion of the upper wall includes one of a resilient member, a bellows or a rolling diaphragm.

5. The manifold assembly of claim 1, further including a stand-off device.

6. The manifold assembly of claim 5, wherein:
the rigid conduit includes a body;
the rigid conduit body includes a second end;
the rigid conduit body second end disposed in the manifold body enclosed space;
the stand-off device is disposed on the rigid conduit body second end; and
the stand-off device is one of a cage or a number of protrusions.

7. The manifold assembly of claim 1, wherein the second opening is not substantially circular.

8. A manifold assembly for a patient interface device, the manifold assembly comprising:
a manifold body including an elastic portion;
a rotational coupling including a rigid conduit, wherein the rigid conduit is rotatably coupled to the manifold body elastic portion, wherein the rotational coupling and the elastic portion form a motion decoupling assembly, and wherein the motion decoupling assembly decouples the remaining portions of the manifold body from external forces applied to the rigid conduit;
wherein the manifold body is elongated and defines a generally enclosed space, the manifold body includes an upper wall;
wherein the elastic portion is disposed on the upper wall;
wherein the manifold body further includes a first opening and a second opening;
wherein the first opening is disposed on the elastic portion of the upper wall;
wherein the rigid conduit includes a substantially circular cross-section;
wherein the rigid conduit is rotatably coupled to the first opening;
a stand-off device;
wherein the manifold body includes a lower wall, an inner surface and a collar;
wherein the collar includes an, inner, second end disposed within the manifold body enclosed space;
wherein the manifold body lower wall and collar second end are part of the manifold body inner surface;
wherein the stand-off device is disposed on the manifold body inner surface adjacent the first opening; and
wherein the manifold body stand-off device includes a number of intermittent protrusions extending from one of the manifold body lower wall or collar second end.

9. A respiratory interface device comprising:
a patient interface device tubing assembly including a number of tubular members, each tubular member including a first end and a second end;
a manifold assembly including a manifold body and a rotational coupling;
the manifold body including an elastic portion wherein the elastic portion is more flexible than the other portions of manifold body;
the rotational coupling including a first opening and a rigid conduit, the first opening disposed on the elastic portion;
the manifold body further including a second opening;
a tubular member first end coupled to the second opening;
the rigid conduit rotatably coupled to the manifold body elastic portion;
the rotational coupling and the elastic portion forming a motion decoupling assembly;
the motion decoupling assembly decoupling the remaining portions of the manifold body from external forces applied to the rigid conduit;
the manifold body is elongated and defines a generally enclosed space, the manifold body includes an upper wall;
the elastic portion being disposed on the upper wall;
the first opening being disposed on the elastic portion of the upper wall;
the rigid conduit including a substantially circular cross-section; and
the rigid conduit being rotatably coupled to the first opening.

10. The respiratory interface device of claim 9, wherein:
the rotational coupling includes a conduit assembly;
the conduit assembly includes a hub;
the hub includes an axis of rotation, an outer radial surface and a radial inner surface;
the hub inner surface is substantially circular;
the rigid conduit outer surface includes a substantially circular outer surface;
the rigid conduit outer surface corresponds to the hub inner surface;
the hub is fixed to a medial portion of the upper wall; and
the rigid conduit is rotatably coupled to the hub.

11. The respiratory interface device of claim 10, wherein the first opening snuggly corresponds to the hub outer radial surface.

12. The respiratory interface device of claim 9, wherein the elastic portion of the upper wall includes one of a resilient member, a bellows or a rolling diaphragm.

13. The respiratory interface device of claim 9, further including a standoff device.

14. The respiratory interface device of claim 13, wherein:
the rigid conduit includes a body;
the rigid conduit body includes a second end;
the rigid conduit body second end disposed in the manifold body enclosed space;
the stand-off device is disposed on the rigid conduit body second end; and
the stand-off device is one of a cage or a number of protrusions.

15. The respiratory interface device of claim 9, wherein the second opening is not substantially circular; and each tubular member is not substantially circular.

16. A respiratory interface device comprising:
a patient interface device tubing assembly including a number of tubular members, each tubular member including a first end and a second end;
a manifold assembly including a manifold body and a rotational coupling;
the manifold body including an elastic portion;
the rotational coupling including a first opening and a rigid conduit, the first opening disposed on the elastic portion;
the manifold body further including a second opening;
a tubular member first end coupled to the second opening;
the rigid conduit rotatably coupled to the manifold body elastic portion;
the rotational coupling and the elastic portion forming a motion decoupling assembly;
the motion decoupling assembly decoupling the remaining portions of the manifold body from external forces applied to the rigid conduit;
the manifold body is elongated and defines a generally enclosed space, the manifold body includes an upper wall;
the elastic portion is disposed on the upper wall;
the first opening is disposed on the elastic portion of the upper wall;
the rigid conduit including a substantially circular cross-section;
the rigid conduit is rotatably coupled to the first opening;
a standoff device,
the manifold body includes a lower wall, an inner surface and a collar;
the collar includes an, inner, second end disposed within the manifold body enclosed space;
the manifold body lower wall and collar second end are part of the manifold body inner surface;
the stand-off device is disposed on the manifold body inner surface adjacent the first opening; and
the manifold body stand-off device includes a number of intermittent protrusions extending from one of the manifold body lower wall or collar second end.

* * * * *